(12) United States Patent
Vija et al.

(10) Patent No.: US 6,950,494 B2
(45) Date of Patent: Sep. 27, 2005

(54) METHOD FOR CONVERTING CT DATA TO LINEAR ATTENUATION COEFFICIENT MAP DATA

(75) Inventors: A. Hans Vija, Evanston, IL (US); Vladimir Desh, Buffalo Grove, IL (US)

(73) Assignee: Siemens Medical Solutions, USA, Malvern, PA (US)

( * ) Notice: Subject to any disclaimer, the term of this patent is extended or adjusted under 35 U.S.C. 154(b) by 103 days.

(21) Appl. No.: 10/660,275

(22) Filed: Sep. 11, 2003

(65) Prior Publication Data

US 2005/0058259 A1 Mar. 17, 2005

(51) Int. Cl.⁷ .......................... A61B 6/02; G01N 23/083
(52) U.S. Cl. ............................. 378/62; 378/4; 378/8; 378/901
(58) Field of Search ........................... 378/4, 8, 15, 19, 378/62, 63, 901

(56) References Cited

U.S. PATENT DOCUMENTS

2004/0264626 A1 * 12/2004 Besson .......................... 378/4
2004/0264627 A1 * 12/2004 Besson .......................... 378/5
2004/0264628 A1 * 12/2004 Besson .......................... 378/5

* cited by examiner

*Primary Examiner*—David V Bruce (57) ABSTRACT

A method for converting output data from a computer tomography (CT) device to linear attenuation coefficient data includes a step of receiving output pixel data from a CT device for a pixel of a CT image. The value of the pixel data is compared to a predetermined range. If the value is within the predetermined range, a linear attenuation coefficient is calculated from the pixel data using a first conversion function corresponding to said predetermined range. If the value is outside the predetermined range, the linear attenuation coefficient is calculated from the pixel data using a second conversion function corresponding to a range outside said predetermined range. The calculated coefficient is stored in a memory as part of a linear attenuation coefficient map.

53 Claims, 11 Drawing Sheets

"EFFECTIVE" TRANSMISSION ENERGY (keV)

FIG. 14

DIFFERENCE IN EFF. ENERGY FROM TRUE EFFECTIVE ENERGY (%)

METHOD FOR CONVERTING CT DATA TO LINEAR ATTENUATION COEFFICIENT MAP DATA

BACKGROUND OF THE INVENTION

1. Field of the Invention

This invention generally pertains to systems and methods for analyzing computer tomography data. More particularly, the present invention is directed to a method of converting computer tomography (CT) data to linear attenuation coefficient data for use in nuclear medicine, such as to compensate for attenuation in SPECT and PET imaging.

2. Description of the Related Art

Medical imaging falls into two distinct modalities or types. Transmission imaging refers to imaging such as X-ray imaging where the imaging source (e.g., X-ray) is external to the subject and is transmitted through the subject to a detector. Emission imaging refers to imaging where the imaging source (e.g., gamma-emitting radiopharmaceutical) is internal to the subject (as a result of injection or ingestion) and is emitted from the subject to a detector. Attenuation of source radiation occurs when the source radiation passes through the subject tissue, as a result of the subject absorbing or scattering some of the radiation photons. In general it is a simple matter to determine the attenuation of a discrete transmission source, since the amount of the external source being transmitted through the subject is known, and can be compared with the amount of radiation exiting the subject. However, measurement of attenuation in emission imaging is more difficult, because the accurate amount of emission source radiation being generated in the subject that results in a quantity of radiation being detected outside the subject cannot be measured directly.

Appropriate corrections for scatter and attenuation correction are prerequisites for quantitative nuclear medicine. X-ray CT image volumes can be used to derive Linear Attenuation Coefficient (LAC) maps ("mu-maps"), suitable for compensating for attenuation in single-photon-emission-computer-tomography (SPECT) and positron-emission-tomography (PET).

In general, a transmission scan is performed at an energy level other than the energy of the emission scan. Thus, the resulting attenuation map needs to be scaled to the actual emission energy of the scan, before it can be used to correct for attenuation in the emission reconstruction process. For source-based derived mu-maps, the conversion is simple because the discrete transmission and emission energies are known. For x-ray CT however, the transmission spectrum is continuous (and not discrete as it is the case for source-based methods), and, more importantly, depends upon the particular CT scanner and the attenuating body.

Figure 1:
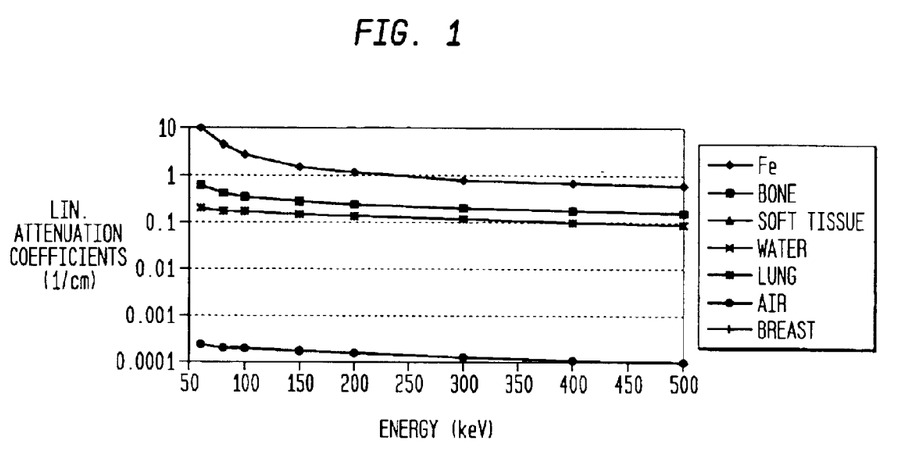
FIG. 1 shows linear attenuation coefficients for different types of tissue and their dependencies on the energy of the photons.

FIG. 1 shows that attenuation coefficients for different types of tissue depend on the energy of the photons, and can be grouped in essentially four groups, depending on their atomic number, Z: Air, soft tissue, bone, and iron, with iron representing a class of "Very High-Z" implants, such as surgical screws, hip-replacements, or other possible very high-Z materials in the body.

X-ray CT images are calibrated so that each voxel is measured in units of Hounsfield, usually defined as:

$$HU^{Material} = (\mu_T^{Material} - \mu_T^{Water})/(\mu_T^{Water} - \mu_T^{Air}) * 1000 \quad (1.),$$

Figure 16:
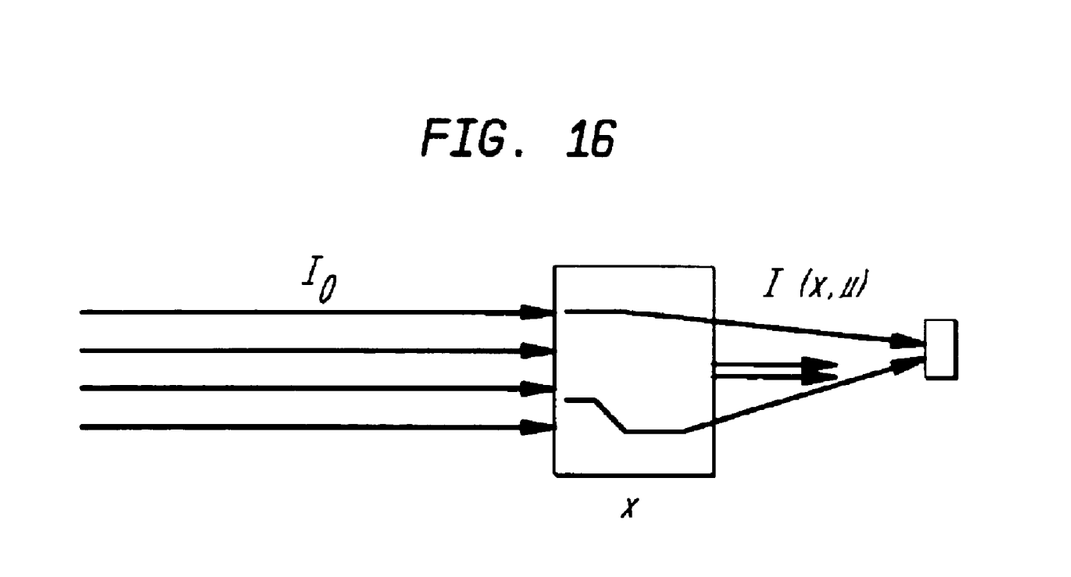
FIG. 16 is a diagram of a collimator showing "broad beam" attenuation of initial flux.

In this definition $\mu_T^{Material}$ is the linear attenuation coefficient of a given material at an "effective" transmission energy T, and $\mu_T^{Water}$ is the linear attenuation coefficient of water at the same "effective" transmission energy T. The linear attenuation coefficients are "narrow beam" values, which are derived from primary photon counts only, and thus do not include any scattered photons (see also FIG. 16).

Because a CT scanner emits a continuous spectrum of x-rays, an "effective" transmission energy is not easily obtained. The HU values are normalized for all scanners and protocols if the CT scanner for clinical practice has been properly set-up, so that water always corresponds to HU=0 and air corresponds to HU=−1000 (it is noted that some definitions multiply by a factor of $2^{10}$=1024; such cases are included within the scope of the invention). All clinical CT scanners have to be calibrated using a vendor specific protocol to conform to this definition. However, there is no definition for densities greater than water. For instance, the same bone tissue may have different HU values when acquired with different CT scanners. The HU value of a bone specimen may even change depending on the surrounding amount of soft tissue and reconstruction parameters on the same CT scanner. Converting bone tissue accurately is important because it may contribute largely to attenuation of emission energy.

Various approaches are known for converting CT values to linear attenuation coefficients, depending on the degree and type of approximation treating the continuous CT spectrum. These methods can be grouped in two major classes: Uniform scaling, and Non-uniform scaling.

In Uniform scaling, all pixels in the transmission slices are multiplied by the same factor K, where K is usually computed from the linear attenuation coefficient of water at the effective transmission-energy T $\mu_T^{Water}$ and emission-energy E $\mu_E^{Water}$:

$$K = \mu_E^{Water} / \mu_T^{Water} \quad (2).$$

This approach is accurate for soft tissues (low Z), since their attenuation properties are similar to water. In water, or other low-Z materials, Compton scattering is the dominant effect for clinically used emission energies, but for high-Z materials such as bone, the photoelectric absorption becomes the dominant effect. As a result, a scaling factor derived using water deviates considerably from a bone-derived scaling value. Thus, equation (2) provides inaccurate linear attenuation coefficients for materials more dense than water and soft tissue. The equation also assumes that an "effective" transmission-energy is known.

For a CT scan, the transmission energy can only be an "effective" transmission-energy, which essentially replaces the continuous transmission spectrum through the body with a mono-energetic "effective" transmission-energy. However, such an effective transmission-energy depends on the type of CT scanner, patient, and also on the CT reconstruction parameters. Examples of such methods are described in Kalki K., Brown, J. K.,et al., "Myocardial Perfusion Imaging with a Correlated X-ray CT and SPECT System: An Animal Study", IEEE TNS, 43(3), 1996, pp. 2000–2007, 1996, which is incorporated herein by reference.

Non-Uniform Scaling Tissue method allows regions of the CT image volume to be defined as part of different classes of tissues ("segmentation"). Either each class of tissue is scaled from some "effective" transmission energy to the emission energy, or pixel values for each tissue type are replaced with the appropriate attenuation coefficients at the emission energy. Typical choices for tissue types include soft tissue, bone, lung and air. However, there are numerous problems with this approach. For example, this method does not take into account existing variations in tissues densities for the same tissue classes, it is limited to the errors of the segmentation routine, it may require an educated user to segment the data accurately, and it is not user-friendly.

Pixel-by-pixel conversion is an extension of the tissue typing approach. In this method, each pixel is scaled from CT units to linear attenuation coefficients. In principle, this method requires knowledge of the type of tissue for each pixel. This is often difficult because pixels may contain more than one tissue type ("partial volume"), or an educated user may be needed to identify the tissue type of each pixel (see, D. R. White, M. Fitzgerald, "Calculated attenuation and Energy Absorption Coefficients for ICRP Reference Man (1975) Organs and Tissues", Health Physics, 33, pp. 73–81, 1977, which is incorporated herein by reference). Therefore, this method suffers from similar problems.

Thus, there is a need for new and improved systems and methods for creating linear attenuation coefficient maps from CT image data that improve upon and solve the foregoing problems with the prior art.

SUMMARY OF THE INVENTION

In accordance with the foregoing and other objects, the present invention provides systems and methods for converting CT data to a linear attenuation coefficient map for use in nuclear medicine.

According to one embodiment of the present invention, a simple method is provided for converting CT images obtained from an arbitrary clinical CT scanner to "mu-maps". This method adapts to patient specific data and the varying parameters of the CT scan and reconstruction, and thus eliminates the need for any additional calibrations, other than the clinically necessary, vendor specific CT scanner calibrations. The present invention represents an optimal trade-off between accuracy and simplicity.

The present invention provides a number of non-limiting advantages. For example, the present invention is capable of the following:

converting to emission energies from 50 keV to 511 keV within a similar accuracy range;

modeling the energy dependence of tissues accurately over the whole clinically used emission energy range (50, 511) keV;

estimating from the clinical CT images an effective energy;

converting to an effective emission energy in the case of multiple emission peaks; and adjusting the linear attenuation map to the acquisition window size in the emission scan.

According to an embodiment of the present invention, a method is provided for converting output from a computer tomography (CT) device to a linear attenuation coefficient map. The method includes the steps of receiving output pixel data from a CT device for a pixel of a CT image; comparing a value of the pixel data to a predetermined range; if the value is within the predetermined range, calculating a linear attenuation coefficient from the pixel data using a first function; if the value is outside the predetermined range, calculating the linear attenuation coefficient from the pixel data using a second function; and storing said calculated coefficient in a memory as part of a linear attenuation coefficient map.

According to an embodiment of the present invention, a method is provided for converting output from a computer tomography (CT) device to a linear attenuation coefficient map. The method includes the steps of: receiving output pixel data from a CT device for each pixel of a CT image and for each pixel: comparing a value of the pixel data to a predetermined range; if the value is within the predetermined range, generating a first function and calculating a linear attenuation coefficient from the pixel data using the first function; and if the value is outside the predetermined range, generating a second function and calculating a linear attenuation coefficient from the pixel data using the second function; and generating a linear attenuation coefficient map based upon each linear attenuation coefficient calculated for each pixel.

According to an embodiment of the present invention, a system is provided for generating a linear attenuation coefficient map. The system includes an input, a processing unit and an output. The input is for receiving pixel data. The processing unit is configured to compare a value of the pixel data to a predetermined range, to select a function based on whether the value is within the predetermined range or outside the predetermined range, and to calculate a linear attenuation coefficient from the pixel data using the selected function. The output is for outputting the calculated linear attenuation coefficient.

According to an embodiment of the present invention, a computer program product is provided which resides on a computer readable medium, for interactively constructing, editing, rendering and manipulating pixel data for a CT image. The computer program includes a computer executable instructions for causing the computer to perform the following: receiving output pixel data from a CT device for a pixel of a CT image; comparing a value of the pixel data to a predetermined range; if the value is within the predetermined range, calculating a linear attenuation coefficient from the pixel data using a first function; if the value is outside the predetermined range, calculating the linear attenuation coefficient from the pixel data using a second function; and storing the calculated coefficient in a memory as part of a linear attenuation coefficient map.

With these and other objects, advantages and features of the invention that may become hereinafter apparent, the nature of the invention may be more clearly understood by reference to the following detailed description of the invention, the appended claims, and the drawings attached hereto.

BRIEF DESCRIPTION OF THE DRAWINGS

The invention will be described in detail with reference to the following drawings, in which like features are represented by common reference numbers and in which.

DETAILED DESCRIPTION OF THE PREFERRED EMBODIMENT

Figure 2:
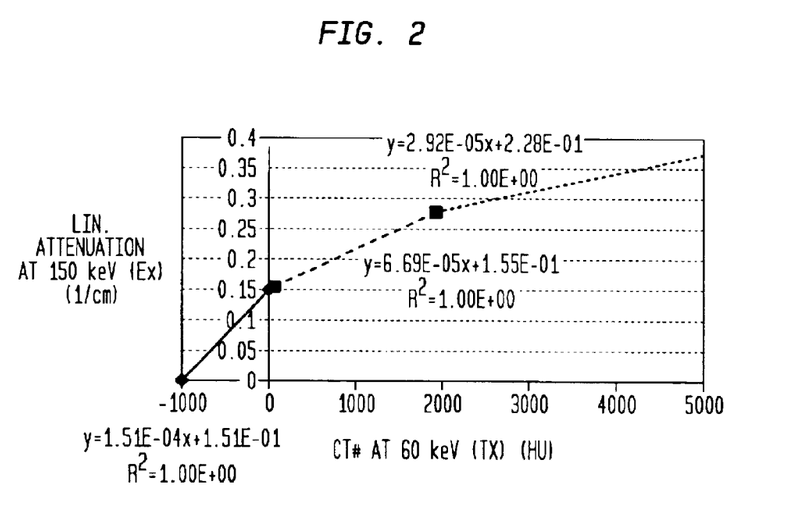
FIG. 2 is a typical interpolated graph demonstrating the relationship between CT's Hounsfield Units (HU) and linear attenuation coefficients.
Figure 3:
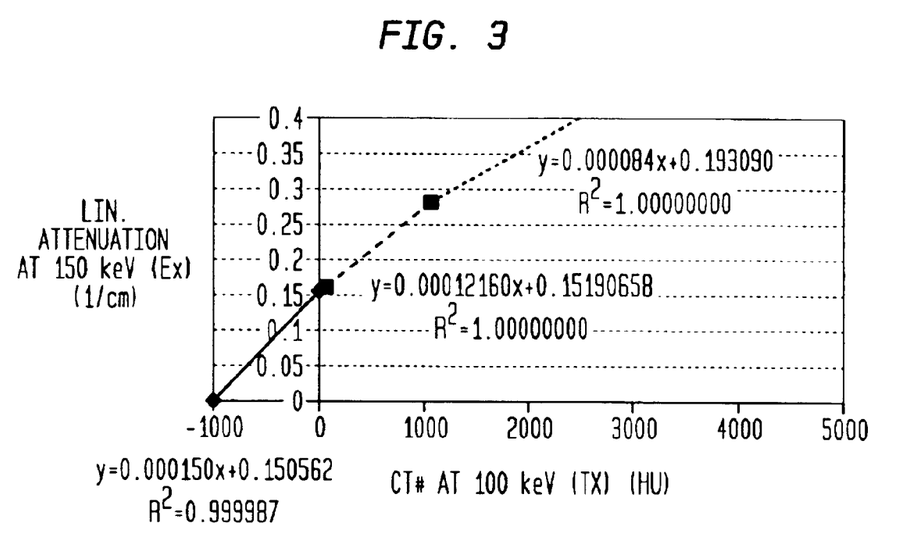
FIG. 3 is a typical conversion graph from HU to linear attenuation coefficients at 100 keV transmission energy and 150 keV emission energy.
Figure 4:
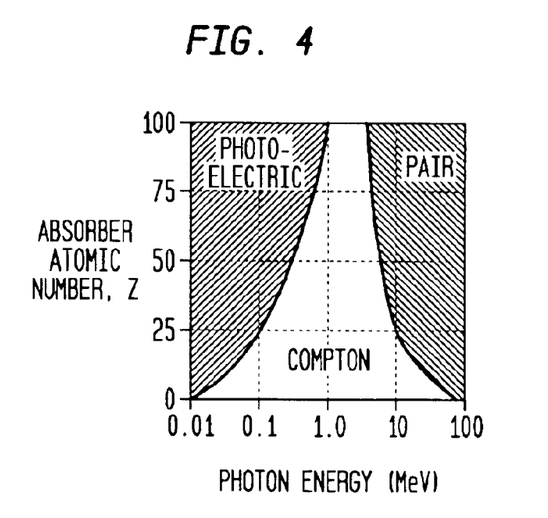
FIG. 4 is a graph showing the most prominent interaction for biological materials and relevant energies.

A typical interpolated graph demonstrating the relationship between CT's Hounsfield Units (HU) and linear attenuation coefficients is shown in FIG. 2. The conversion from HU to linear attenuation coefficients is dependent upon emission-energy and transmission-energy. For instance, a CT image acquired at two different effective transmission energies ("tx"), will need to be scaled differently to the same emission energy, as can be seen by comparing FIG. 2 and FIG. 3. This difference in scaling occurs because of the different physical effects that contribute for varying energies at various amounts to the attenuation. For energies below 511 keV, the attenuation can be considered as a combination of both Compton scattering and photoelectric absorption. But the higher the energy, the lower the contribution of the photoelectric absorption is to the attenuation, and at 511 keV, it is essentially negligible for all biological materials (including bone). In the CT energy range (50–150 keV), however, the photoelectric absorption is not negligible (see FIG. 4 and also see, Sorensen J. A., Phelps M. E., "The Physics of Nuclear Medicine", Grune & Stratton, 1980, which is incorporated herein by reference).

The conversion mechanism used by the present invention is based on the fact that some types of media are always mapped onto certain HU values.

| Air energy | −1000 HU | independent of effective transmission |
|---|---|---|
| Water energy | 0 HU | independent of effective transmission |
| Cortical Bone energy | ~1000–2000 HU | dependent on effective transmission |

Figure 5:
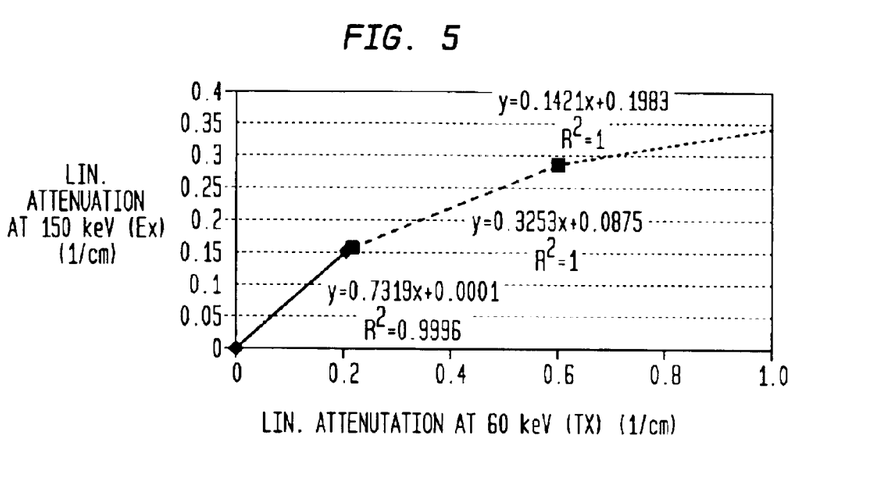
FIG. 5 is a conversion graph from HU to linear attenuation coefficients approximated as piecewise linear functions.

The scaling between the energy dependent linear attenuation coefficient and the HU, which are essentially water normalized differences between the attenuating material and water, can be approximated as piecewise linear functions (see FIG. 5), for the transition between low Z (soft tissue) and higher Z (bone) materials. For water, the linearity is exactly based on the definition of the HU.

For the purposes of the present invention, and without loss of generality, two regions shall be considered: air-to-soft tissue(water) (HU<=0); and soft tissue(water)-to-bone (HU>0).

Figure 6:
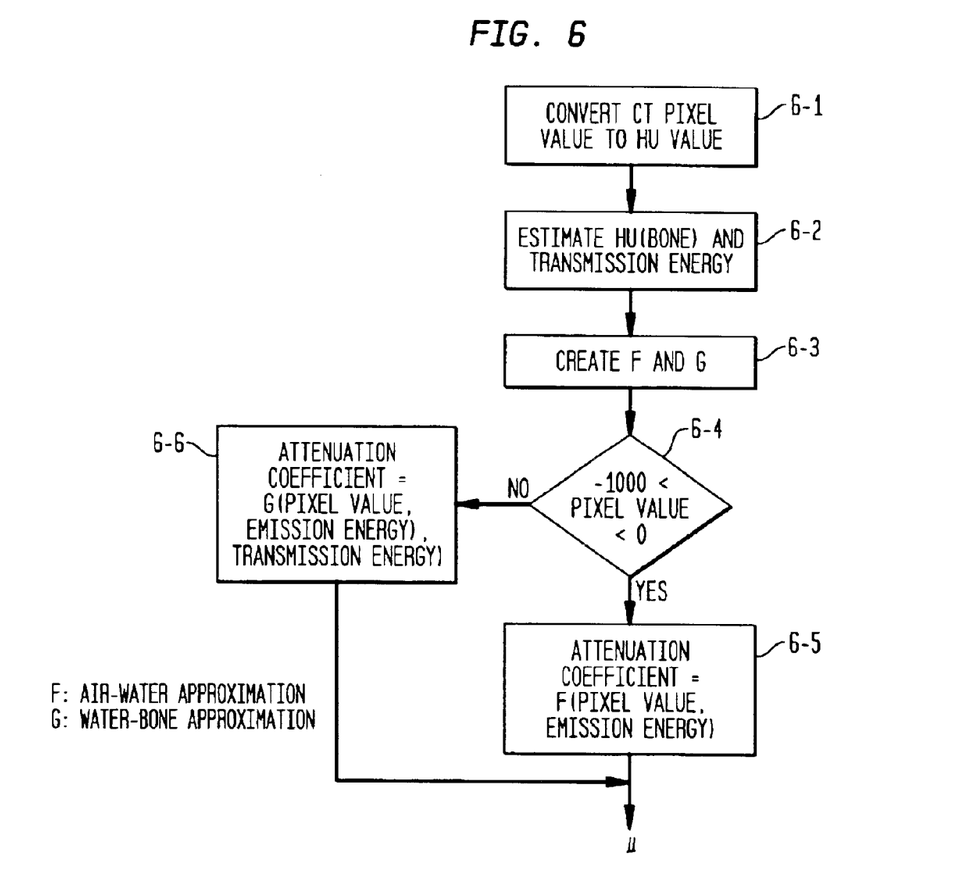
FIG. 6 is a flow diagram of a method for converting from HU to linear attenuation coefficients according to an embodiment of the present invention.

FIG. 6 is a flow diagram of a method of creating a mu-map according to the present invention. It will be understood by those skilled in the art that the following processes may be programmed onto central processor or computer, which may be coupled with a CT scanning device, or which may receive CT data in any fashion. Accordingly, a program written to perform the following may be stored conventionally in memory. Accordingly, the present invention is not limited to any particular system configuration.

Beginning with step 6-1, CT pixel values are converted to HU values. CT devices may output pixel data a number of ways. Typically, a device outputs data in a proprietary fashion that must be converted to HU. The conversion is usually provided by the vendor. For example, CT devices may output DICOM ("Digital Imaging and COmmunication in Medicine" standard) compliant data containing a header that defines the conversion from proprietary pixel data to HU. Obviously, if a CT device outputs pixel values as HU values, then the conversion is unity.

At step 6-2, HU (bone) and the effective transmission energy are estimated. In one embodiment of the present invention, a simple "numerical observer" replaces the educated human observer. However, it is to be noted that the present invention also applies to more sophisticated numerical observers, using e.g. Artificial intelligence, data base scoring, statistical methods, etc. One implementation of such a "numerical observer" uses the histogram of the CT image volume to find the most common bone HU value at the given scan parameters in the CT image volume. This value is assigned to be $HU_T^{Bone}$, where the sub-script "T" indicates that this value is at some "effective" CT transmission energy. This "effective" CT transmission energy includes all possible effects that could influence the bone-HU, including effects from, e.g., the CT reconstruction filter.

Figure 12:
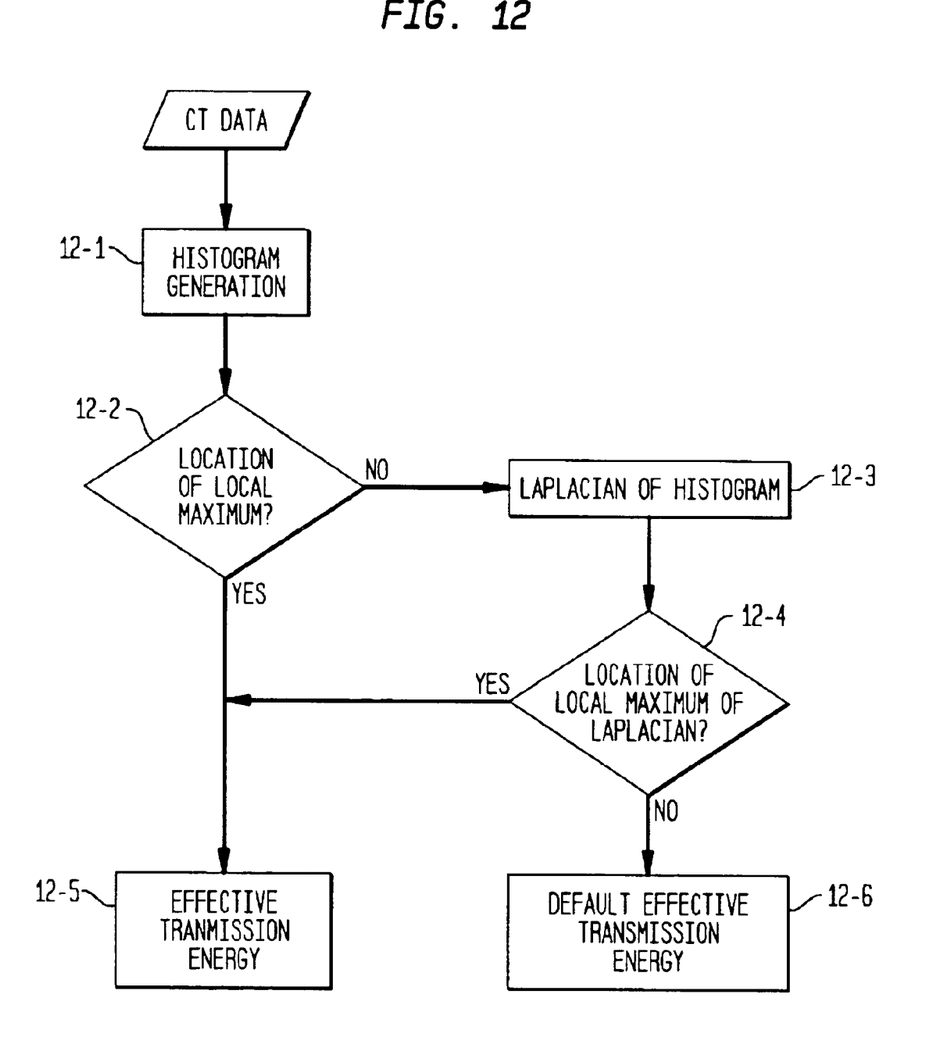
FIG. 12 is a flow diagram of a method for computing the effective transmission energy, according to an embodiment of the present invention.

A flow diagram of the "numerical observer" is shown in FIG. 12. At step 12-1, the histogram is generated from the CT data for the entire CT image, by conventional means. The histogram is binned by HU values and number of pixels per bin. The histogram of a CT image volume of a patient is normally dominated by soft tissue. Bone values span a wide range and the abundance thereof is, in general, orders of magnitude less than the abundance of soft tissue values. Hard cortical bone is rather rare and can be found mostly as a shell around the bone structure. Furthermore, bone density decreases with age and is smaller for adolescents than for adults. Thus, it is a real challenge to find the bone value most suitable to set the conversion function from HU to linear attenuation coefficients.

It is assumed that the bone-histogram of a CT image volume of humans can fall in two distinct classes, if the histogram is properly binned: (a) one dominant bone peak (e.g. Head) in the histogram, or (b) no dominant bone peak (e.g. Pelvis).

Figure 7:
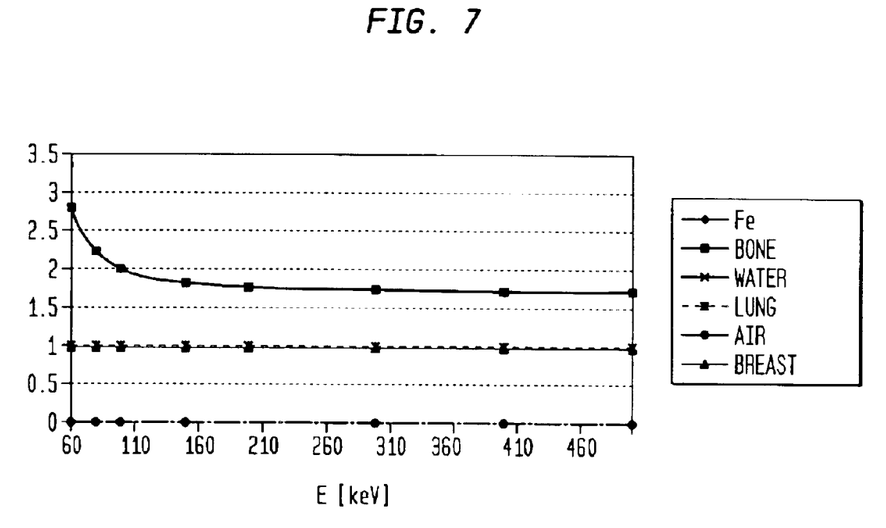
FIG. 7 is a graph of soft tissue normalized attenuation coefficients.

The HU values of bone are clearly larger than zero (0) because the linear attenuation coefficient of bone is, in most cases and for the relevant energies, roughly twice as large as that of water and soft tissue (see FIG. 7; the linear attenuation of bone is roughly 1.75–2 times larger than of water and soft tissue). It is therefore possible to search for the bone peak above a threshold HU-value. The binning parameters of the histogram need to be adjusted to obtain a slowly varying function to search for $HU_T^{Bone}$, yet it needs to be sensitive enough to distinguish between the main sections of the human body with varying amount of bone tissue.

The optimal CT image histogram is preferably binned in N bins in the range ($HU_{Bone,Min}$, $HU_{Bone,Max}$) where the maximum value of the histogram is selected as estimate for $HU_T^{Bone}$. The range ($HU_{Bone,Min}$, $HU_{Bone,Max}$) corresponds to a CT effective energy range of and is chosen to include all clinical X-ray CT scanners. Other physical effects, such as reconstruction filter choice, are essentially included into this value.

At step 12-2, the location of the local maximum value (dominant bone peak) is determined. If there is a dominant bone peak, then the location of the dominant bone peak is used as the estimated $HU_T^{bone}$. If there is no local maximum, then at step 12-3 the Laplacian (i.e., $2^{nd}$ derivative) of the histogram is generated. Then, at step 12-4, the location of the local maximum value of the Laplacian is determined. If there is a local maximum, it is used as the estimated $HU_T^{bone}$.

Figure 8:
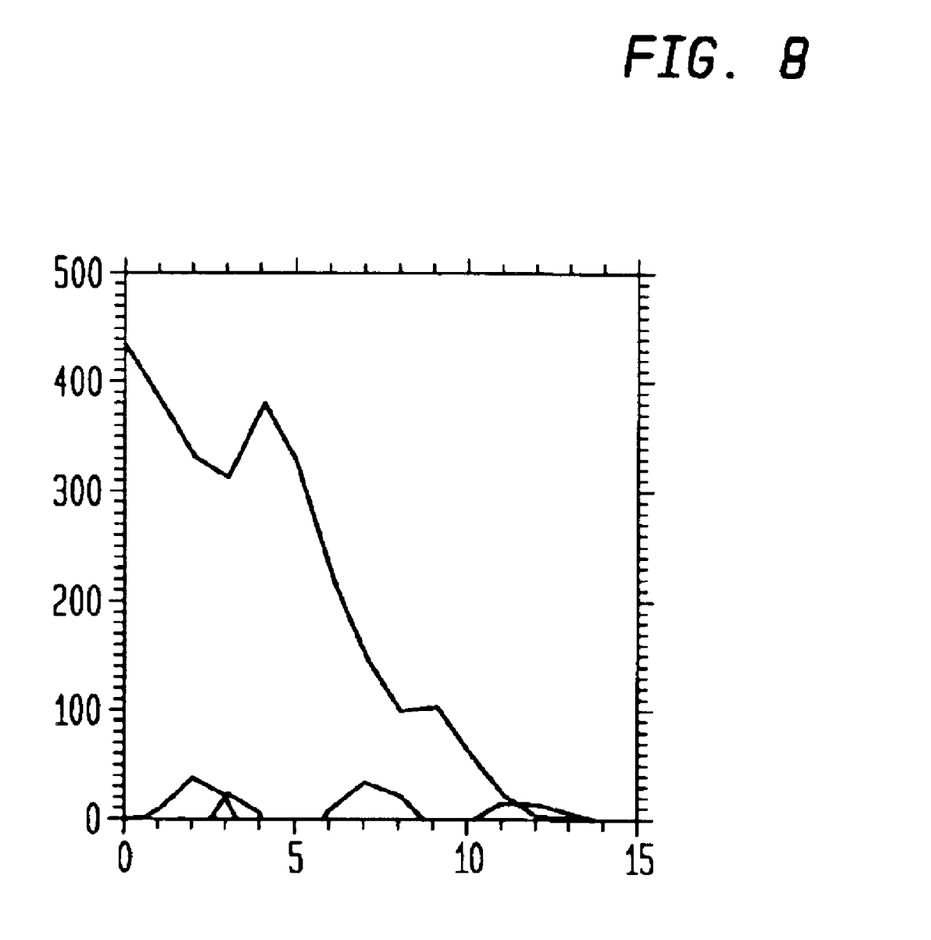
FIGS. 8a–8b are a slice of CT of a torso region and a corresponding histogram.
Figure 9:
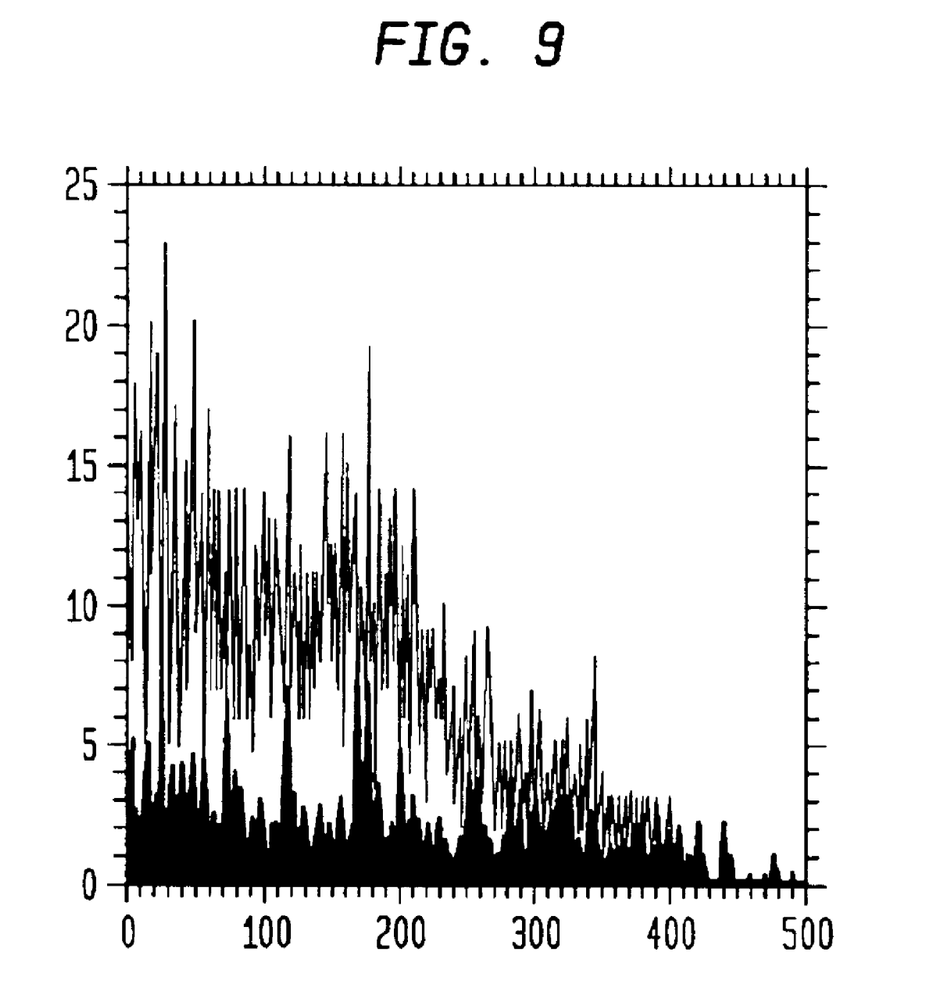
FIG. 9 is a histogram of the CT volume of FIG. 8b at a resolution of 500 bins.
Figure 10:
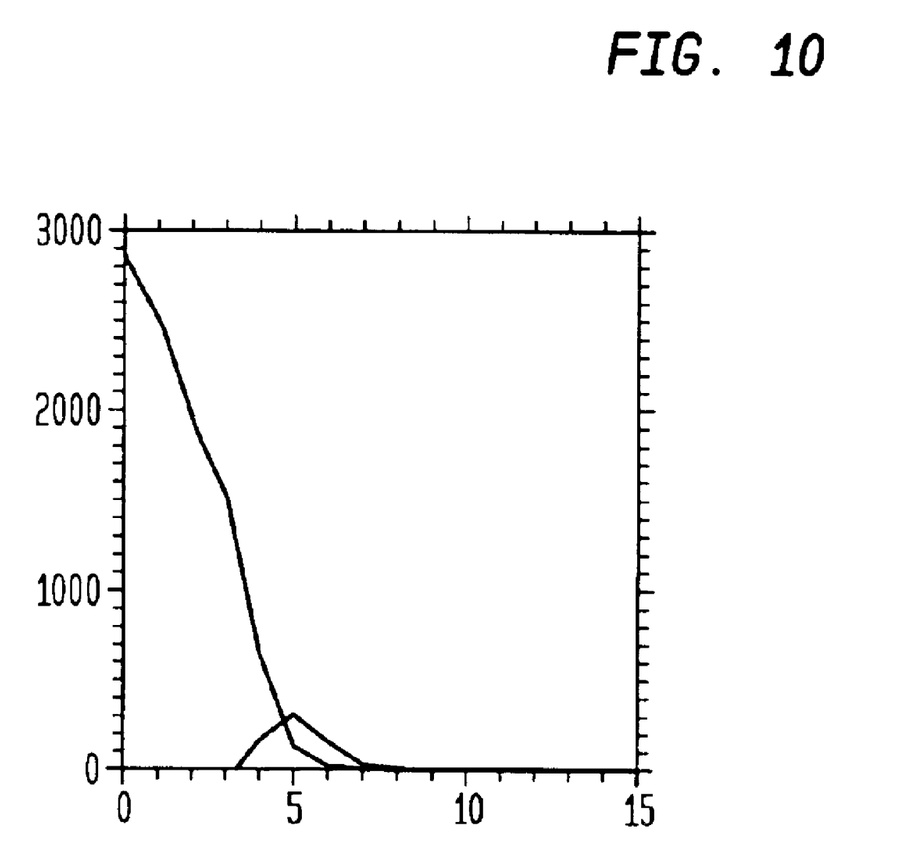
FIGS. 10a–10b are a slice of CT of a pelvis region and a corresponding histogram.
Figure 11:
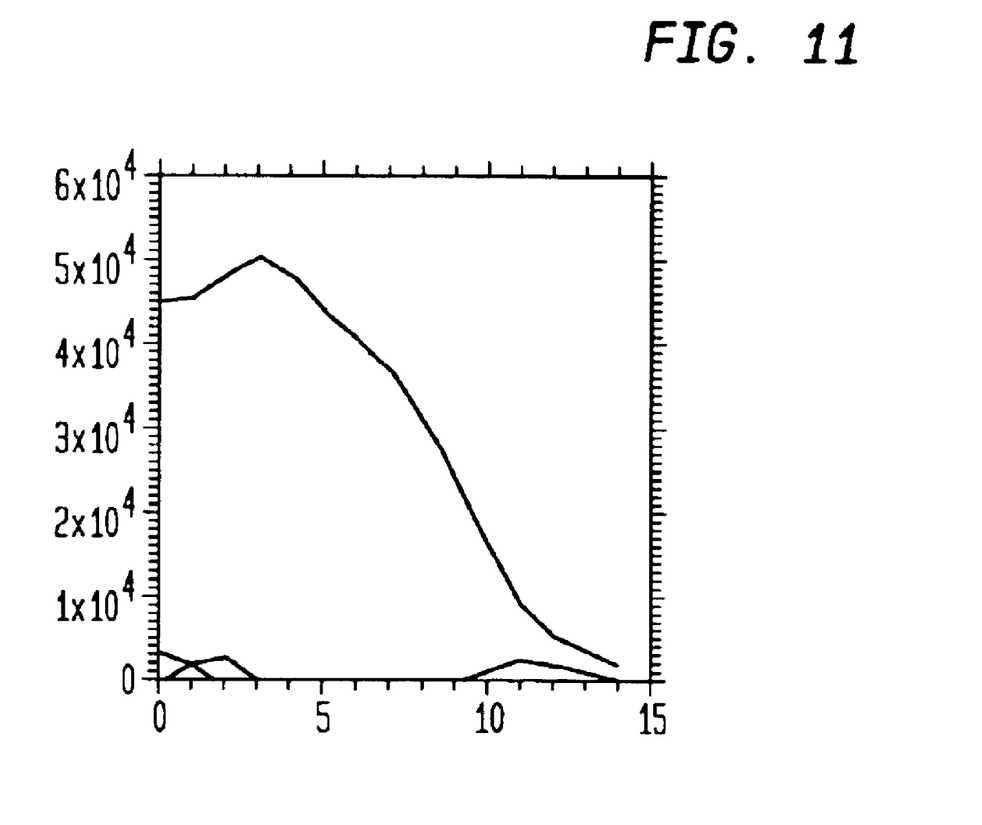
FIGS. 11a–11b are a slice of CT of a skull region and a corresponding histogram.

As examples, FIGS. 8b and 8a, respectively show a slice of the torso region (Kidney) and the histogram, binned with parameters. The lower curves show first and second derivatives. In this case a peak is clearly present representing a range of HU value, corresponding to the most prevalent bone structure. The kidney stone is rather small and localized and is represented as the second peak at higher HU units, which is not used to derive the effective energy. FIG. 9 shows the histogram with a rather fine binning, showing the values for bone vary strongly. These figures shows how 'noisy' the data is. The lower curves show first and second derivatives. It would be very difficult to find the most relevant bone value from this histogram. FIGS. 10a–10b and 11a–11b show slice and histograms of other regions of the body, representing the most common bone value distributions, which can be analyzed with the "numerical observer" of the present invention. In FIGS. 10a–10b, The lower curve shows the second derivative. The location of the maximum of the second derivative is used to estimate the highest reasonable bone value. No distinct bone peak. In FIGS. 11a–11b, note the distinct, but wide, bone peak from the skull region. The lower curves show the first and second derivatives.

Once the most likely value of bone tissue $HU_T^{Bone}$ in the CT image volume is estimated, this value can be used to estimate the "effective" CT transmission energy using equations (1) and (2). First, equations (1) and (2) are used to find $\mu_E^{Bone}$ corresponding to the estimated $HU_T^{Bone}$ as follows:

$$HU_T^{Bone}=(\mu_T^{Bone}-\mu_T^{Water})/(\mu_T^{Water}-\mu_T^{Air})*1000; \quad (3)$$

$$\mu_E^{Bone}/\mu_T^{Bone}=(a_{bone}*E^b{}_{bone}+c_{bone})/(a_{bone}*T^b{}_{bone}+c_{bone})=K^{Bone}(E,T). \quad (4)$$

Here (3) is the Hounsfield expression for bone tissue, $a_{bone}$, $b_{bone}$, and $c_{bone}$ are bone coefficients from a fit, and E and T are user-defined emission and estimated transmission energies. Combining (3) and (4), $\mu_E^{Bone}$ is expressed through $HU_T^{Bone}$ as:

$$\mu_E^{Bone}=K^{Bone}(E,T)*((HU_T^{Bone}/1000)*(\mu_T^{Water}-\mu_T^{Air})+\mu_T^{Water}). \quad (5)$$

The effective transmission energy T is solved from $\mu_E^{Bone}$ with a, b, c being known for bone and water.

Figure 13:
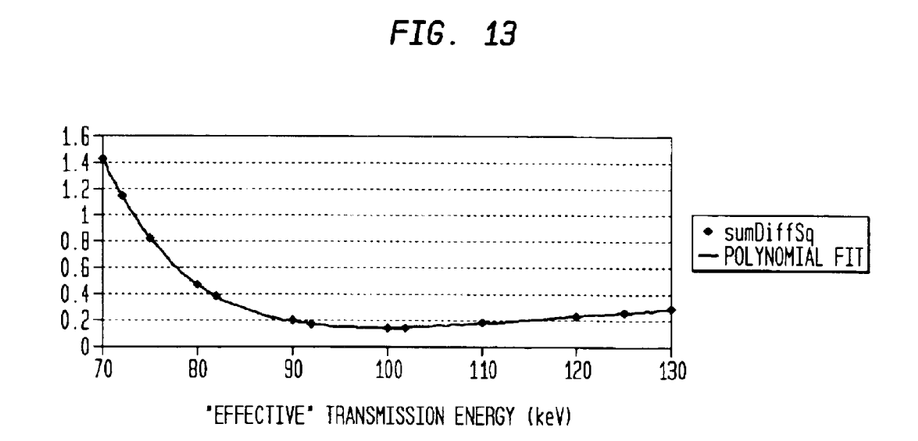
FIG. 13 is a chart of the optimal default effective transmission energy, according to an embodiment of the present invention.

Even if no appropriate bone value is found, the CT effective energy needs to be determined. Accordingly, if there is no local maximum, then a default effective transmission energy is selected at 12-6. An error analysis allows the computation of the optimal default energy, which minimizes the error of the conversion (see FIG. 13).

Once the effective transmission energy is determined at step 6-2, conversion functions F and G are created at step 6-3. The energy dependence of the linear attenuation coefficient can be fitted by a double-power law, with coefficients a, b, c for energies below and above a transition energy $E_{TH}$:

$$\mu(E)=a<E^{b<}+c< \text{ for } E\leq Eth;$$

$$\mu(E)=a>E^{b>}+c> \text{ for } E\geq Eth. \quad (2)$$

Above the transition energy, Compton scattering is much more prevalent than photoelectric absorption for low-Z materials. The coefficients a, b, c are "weighted" $X^2$ fit to data (e.g., data published by J. H. Hubbell (see references below) and can be obtained from the National Institute of Standards and Technology, e.g., see www.nist.gov).

The $X^2$ fit is done for below 150 keV, and above 150 KeV, producing two sets of a, b, c values. The $X^2$ fit is "weighted" but not in the usual manner. Weights are typically derived from the variance of the error of a particular data point. In this case, weights have the effect that data points with larger measurement error don't "contribute" as much to the fit as data with a small error. This is used to "nail" the fit at the transition energy better, which in turn gives a fit which is a) continuous in the first derivative for all E in the energy range, and b) has very small deviation from all data points, but in particular at the clinically important energy region around 150 keV. The ratio of the weight at 150 keV with respect to all other weights at the other energy values is 1/10.

The main contribution to the attenuation coefficient comes from the varying cross sections of the photoelectric and Compton effects, which in turn also scale with $Z^x$ and $E^y$ (where x, and y depend on the effect) changes around the chosen transition energy $E_{th}$=150 keV. This transition energy is chosen in part, because in nuclear medicine imaging, 150 keV is close to 140 keV—the TC99 emission energy (Tc99 is very often used in SPECT).

For iron (Fe), the transition energy selected to be 250 keV, which is also fitted in a similar fashion. Although iron is a material that does not normally occur in the body, it is still found in many people (e.g., surgical nails, implants, bullets, wires, etc.), and thus, there is a need to properly compute the linear attenuation coefficient.

The errors of the fit for the mentioned soft tissues and water <0.2% and for bone <0.55% for all energies. The function $a*E^b+c$ is very easy to use, in the subsequent calculations, and is well suited for the purpose.

At step 6-4, it is determined whether the pixel value is between –1000 (HU for air) and 0 (HU for water). If so, processing proceeds to step 6-5. If not, processing proceeds to step 6-6.

At step 6-5, air-soft tissue region is converted using a linear function F, calculated from the data points of air and water, for which the energy dependence is obtained from the above fit to the double-power law (2). Because air and water values on the HU scale are independent of the transmission energy, this conversion is accurate.

Soft tissue-Bone approximation (HU>0) is more difficult. The HU value of bone is scanner, scan, reconstruction, and patient dependent and depends on the effective transmission energy, which is generally unknown. A human observer could identify the bone tissue in a CT volume and assign linear attenuation coefficients to this type of tissue, which is indexed by the HU values.

At step 6-6, a conversion for all other values can then be calculated using the conversion function G for the Soft tissue-Bone region. Function G is approximated by a preferably linear fit to the data from soft-tissue and the identified bone tissue, with the constraint that the conversion function is continuous over the whole HU-range, i.e. F(HU=0)=G(HU=0).

Thus, values for $\mu$ are generated from the pixel values of any x-ray CT imaging device. The generated $\mu$-map may be used in nuclear medicine imagining, such as SPECT and PET.

Estimated Errors

Figure 14:
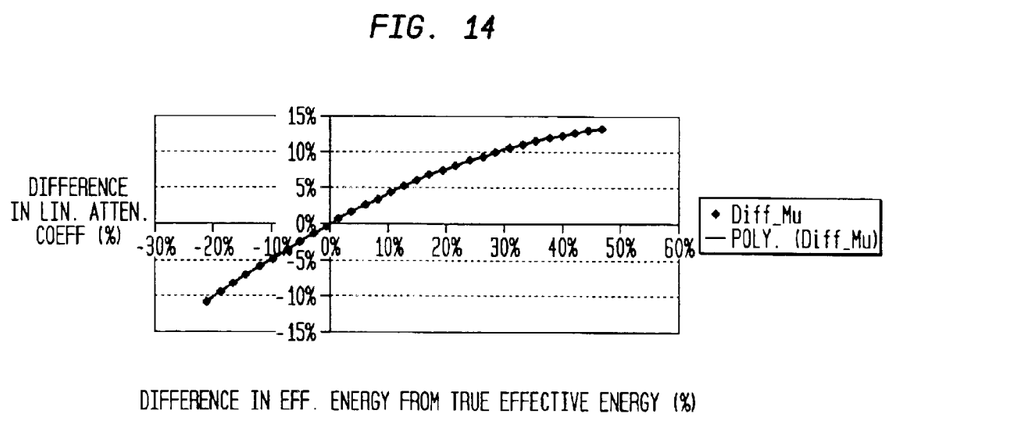
FIG. 14 is a chart showing error estimation of the effective energy, according to an embodiment of the present invention.

Because both F and G functions are pixel value dependant, it makes this approach more accurate than the Tissue Type approach. On the other hand, the fact that two different conversion regions are considered separately makes it more accurate than Uniform Scaling approach. The main limitation of this algorithm, besides small errors caused by linear interpolation of F and G, is due to the uncertainty in CT effective energy for the Water-Bone region. FIG. 14 shows the whole range of possible mis-estimation of the effective transmission energy and the resulting error in the LAC. In general, the effective transmission energy can be estimated within ±10%, and thus can expect the error in the LAC to be roughly ±5%. This can, of course, be improved by calibration measurements.

Multiple Energy Groups for Emission Data

In nuclear medicine application SPECT acquisition may be performed with multiple acquisition windows summed into one projection image. The conversion problem can be generalized to a conversion from the effective transmission energy to the effective emission energy, wherein a discrete spectrum can be replaced by one "effective" emission energy value.

The method to calculate the appropriate effective emission energy can either use a branching-ratio averaged energy or more accurately a weighted $X^2$ fit, which can include n windows. Using the branching-ratio averaged energy method: if the emission energies are $E_i$, with i=1, ..., n, and branching ratios (or mixing ratios) $br_i$, then the "effective" emission energy can be computed using the following equation:

$$E_{eff.emission} = E_1 * br_1 + \ldots + E_n * br_n, \text{ where}$$

$$br_1 + \ldots + br_n = 1.$$

This formula is only an approximation, but the errors are usually less than 1%. A more accurate method is obtained by $X^2$-fit having fit parameters that are the effective narrow beam linear attenuation coefficient and un-attenuated counts. The $X^2$-fit results are more accurate and preferred.

Compensation for Acquisition Window Width

In practice, SPECT projection data always contains object scatter, due to necessary large size of the acquisition window, and thus, compensating for attenuation in a reconstructing with those "narrow beam" attenuation values, may result in an over-correction. A common method to correct for this problem is to reduce the attenuation values by some factor. This factor depends on the energy of the nuclear medicine image and the acquisition window width (the wider acquisition window the more scatter is detected), which is often neglected. These correction factors are computed from measurements, and a $X^2$-fit can be used to adjust for all possible energies and window widths.

Figure 15:
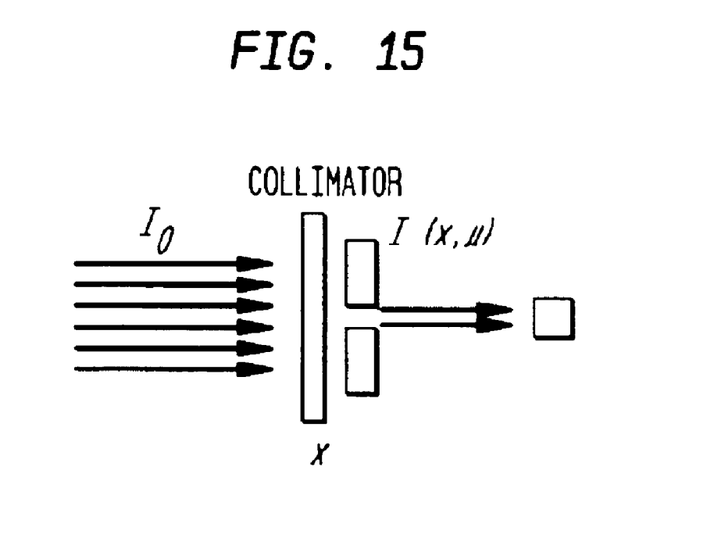
FIG. 15 is a diagram of a collimator showing "narrow beam" attenuation of initial flux.

Attenuation is the effect of detecting less photon flux due to the presence of an attenuating medium. If no medium is present the initial flux is denoted in the following as $I_o$ and in the presence of a material it is denoted as $I(x,\mu)$, where x is the length of the traversed distance of the photons in the material with linear attenuation coefficient $\mu$. The value $I(x, \mu)$ and $I_o$ are related by Beer's law: $I(x,\mu) = I_o e^{-\mu x}$ (see FIG. 15). The linear attenuation coefficient $\mu$ in this equation is assumed not to contain any scatter, and is referred to as the "narrow beam" linear attenuation coefficient.

The difference between "narrow beam" and "broad beam" coefficients is that the first does not include any object scatter, and is the ideal case, the latter does. The name refers to the experimental set-up, where the beam is highly collimated before entering the detector, and thus is a narrow beam, or where it is not collimated and thus is a broad beam (see FIG. 16). Object scatter is allowed to enter the detector, which could be accounted for in an object-dependent build-up factor, not discussed here.

The linear attenuation coefficient $\mu$ is a material property quantifying ability to attenuate radiation. A material of thickness 1 cm and linear attenuation coefficient $\mu$ 11 reduces the initial flux from $I_o$ to $I_o/e^{\mu*1\ cm}$. The unit of the linear attenuation coefficient is 1/cm. The linear attenuation coefficient is energy dependent, where higher energy radiation is more penetrating than lower energy radiation, thus the linear attenuation for a given material is larger (more attenuating) at lower energies than at higher energies. Example:

$\mu_{water}(140\ keV) = 0.15847\ 1/cm < \mu_{water}(70\ keV) = 0.19275\ 1/cm$.

Thus, the invention has been described in connection with what are presently considered to be the most practical and preferred embodiments. However, it is to be understood that the invention is not to be limited to the disclosed embodiments, but, on the contrary, is intended to cover various modifications and equivalent arrangements included within the spirit and scope of the appended claims.

For example, it should be noted that the present invention may be extended to include numerous additional functionality. For example, contrast agents may be handles in a conversion from CT data to linear attenuation coefficients. Other numerical observers may be used to improve the estimation of the effective energy using e.g., CT parameters from DICOM header, Template matching of the CT image volume to a reference CT image of the scanner, Extending the numerical observer to other modalities, such as MRI. Compensation for the acquisition windows width may use the computed narrow beam mu-map to compute a "scatter projection estimate" for the actual acquisition window settings. This scatter projection estimate has the advantage that it is patient dependent and non-local. Mu-maps may be used to classify/segment tissue/voxel types accurately. The results of segmentation may be used for automated analysis of co-registered images from other modalities, e.g. MRI, Angiography, or Ultrasound. The results of segmentation may be used for automatic registration with atlas CT images, improved mutual information registration. Quantitative analysis may be performed on the data and displayed.

For further information, the following references, each of which is incorporated by reference, provide background information and/or details the will assist the reader in understanding the present invention:

Bai C., Shao L, Da Silva A. J. et al., A Generalized Model for the Conversion from CT Numbers to Linear Attenuation Coefficients", IEEE MIC 2002;

Blankespoor S. C., Wu X., et al., "Attenuation Correction of SPECT Using X-ray CT on an Emission Transmission CT System: Myocardial Perfusion Assessment", IEEE TNS, 43(4), 1996, pp. 2263–2274;

Kinahan P. E., Townsend D. W., et al., "Attenuation Correction for a combined 3D PET/CT scanner", Med. Phys. 25(10), 1998, pp. 2046–2053;

Kalki K., Brown J. K., et al., "Myocardial Perfusion Imaging with a Correlated X-ray CT and SPECT System: An Animal Study:, IEEE TNS, 43(3), 1996, pp. 2000–2007;

E. B. Saloman, J. H. Hubbell, and J. H. Scofield, "X-ray Attenuation Cross Sections for Energies 100 eV to 100 keV and Elements Z=1 to Z-92", Atomic Data and Nucl. Data Tables 28, 1 (1988);

Hubbell, J. H. (1982), Photon Mass Attenuation and Energy-Absorption Coefficients from 1 keV to 20 MeV, Int. J. Appl. Radiat. Isot. 33, 1269–1290;

Hubbell, J. H. (1994), Bibliography of Photon Total Cross Section (Attenuation Coefficient) Measurements 10 eV to 13.5 GeV, 1907–1993, NISTIR 5437; and Hubbell, J. H. Gerstenberg, H. M. and Saloman, E. B., Bibliography of Photon Total Cross Section (Attenuation Coefficient) Measurements 10 eV to 13.5 GeV, National Bureau of Standards Internal Report NBSIR 86–3461 (1986), which is incorporated herein by reference.

What is claimed is:

1. A method for converting output data from a computed tomography (CT) device to linear attenuation coefficient data, comprising the steps of:
receiving output pixel data from a CT device for a pixel of a CT image;
comparing a value of the pixel data to a predetermined range;
if said value is within said predetermined range, calculating a linear attenuation coefficient from said pixel data using a first function;
if said value is outside said predetermined range, calculating said linear attenuation coefficient from said pixel data using a second function; and
storing said calculated coefficient in a memory as part of a linear attenuation coefficient map.

2. The method recited in claim 1, wherein said first function is a function independent of a transmission energy related to said pixel data and said second function is a function of said transmission energy.

3. The method recited in claim 1, wherein said first function includes an air-water approximation and said second function includes a water-bone approximation.

4. The method recited in claim 1, further comprising a step of estimating an effective transmission energy associated with said pixel data.

5. The method recited in claim 4, wherein said first function is a function independent of said effective transmission energy and said second function is a function of said effective transmission energy.

6. The method recited in claim 1, further comprising a step of converting said pixel data to Hounsfield units prior to said comparing step.

7. The method recited in claim 1, wherein said predetermined range comprises a range of Hounsfield units for water to Hounsfield units for air.

8. The method recited in claim 4, further comprising the steps of:
generating a histogram for said CT image;
determining a dominant bone peak from said histogram; and
wherein said dominant bone peak is used for estimating said effective transmission energy.

9. The method recited in claim 8, wherein said first function is a function independent of said effective transmission energy and said second function is a function of said effective transmission energy and a value of said dominant bone peak.

10. The method recited in claim 8, wherein said first function varies based upon a relationship between an emission energy related to said pixel and a transition energy.

11. The method recited in claim 8, wherein, if no dominant bone peak is determined, the following additional steps are performed:

calculating a Laplacian of said histogram;
determining a local maximum from said Laplacian;
setting said effective transmission energy based on said local maximum; and
setting said dominant bone peak based on said local maximum.

12. A method for converting output from a computed tomography (CT) device to a linear attenuation coefficient map, comprising the steps of:
receiving output pixel data from a CT device for each pixel of a CT image and for each pixel;
comparing a value of the pixel data to a predetermined range;
if said value is within said predetermined range, generating a first function and calculating a linear attenuation coefficient from said pixel data using said first function; and
if said value is outside said predetermined range, generating a second function and calculating a linear attenuation coefficient from said pixel data using said second function; and
generating a linear attenuation coefficient map based upon each linear attenuation coefficient calculated for each pixel.

13. The method recited in claim 12, wherein said first function is a function independent of a transmission energy related to said pixel data and said second function is a function of said transmission energy.

14. The method recited in claim 12, wherein said first function includes an air-water approximation and said second function includes a water-bone approximation.

15. The method recited in claim 12, further comprising a step of estimating an effective transmission energy associated with said pixel data.

16. The method recited in claim 15, wherein said first function is a function independent of said effective transmission energy and said second function is a function of said effective transmission energy.

17. The method recited in claim 1, further comprising a step of converting said pixel data to Hounsfield units prior to said comparing step.

18. The method recited in claim 12, wherein said predetermined range comprises a range of Hounsfield units for water to Hounsfield units for air.

19. The method recited in claim 15, further comprising the steps of:
generating a histogram for said CT image; and
determining a dominant bone peak from said histogram; and wherein said dominant bone peak is used for estimating said effective transmission energy.

20. The method recited in claim 19, wherein said first function is a function independent of said effective transmission energy and said second function is a function of said effective transmission energy and a value of said dominant bone peak.

21. The method racked in claim 19, wherein said first function varies based upon a relationship between an emission energy related to said pixel and a transition energy.

22. The method recited in claim 19, wherein, if no dominant bone peak is determined, the following additional steps are performed:
calculating a Laplacian of said histogram;
determining a local maximum from said Laplacian;
setting said effective transmission energy based on said local maximum; and setting said dominant bone peak based on said local maximum.

23. A system for generating a linear attenuation coefficient map, comprising:
an input for receiving pixel data;
a processing unit configured to compare a value of the pixel data to a predetermined range, to select a function based on whether said value is within said predetermined range or outside said predetermined range, and to calculate a linear attenuation coefficient from said pixel data using the selected function; and
an output for outputting said calculated linear attenuation coefficient.

24. The system as recited in claim 23, further comprising:
a storage unit coupled with said processing unit and configured to store conversion data.

25. The system as recited in claim 23, wherein said processing unit is further configured to calculate a transmission energy of said pixel data, and wherein if said value is within said predetermined range, said processing unit generates a function that is independent of said transmission energy related to said pixel data, and if said value is outside said predetermined range, said processing unit generates a function that is dependent upon said transmission energy.

26. The system recited in claim 23, wherein if said value is within said predetermined range, said processing unit generates a function that includes an air-water approximation, and if said value is outside said predetermined range, said processing unit generates a function that includes a water-bone approximation.

27. The system as recited in claim 23, wherein said processing unit is further configured to estimate an effective transmission energy associated with said pixel data.

28. The system as recited in claim 27, wherein said processing unit converts said pixel data to Hounsfield units.

29. The system as recited in claim 27, wherein said predetermined range comprises a range of a Hounsfield units value for water to a Hounsfield units value for air.

30. The system as recited in claim 27, wherein said pixel data corresponds to a CT image from a CT device, said processing unit is further configured to generate a histogram for said CT image, determine a dominant bone peak from said histogram, and use said dominant bone peak for estimating said effective transmission energy.

31. The system as recited in claim 30, wherein if said value is outside said predetermined range, said processing unit generates a function based on said effective transmission energy and a value of said dominant bone peak.

32. The system as recited in claim 30, wherein if said value is inside said predetermined range, said processing unit generates a function based upon a relationship between an emission energy related to said pixel and a transition energy.

33. A computer program product, residing on a computer readable medium, for interactively constructing, editing, rendering and manipulating pixel data for a CT image, said computer program comprising computer executable instructions for causing the computer to perform the following:
receiving output pixel data from a CT device for a pixel of a CT image;
comparing a value of the pixel data to a predetermined range;
if said value is within said predetermined range, calculating a linear attenuation coefficient from said pixel data using a first function;
if said value is outside said predetermined range, calculating said linear attenuation coefficient from said pixel data using a second function; and
storing said calculated coefficient in a memory as part of a linear attenuation coefficient map.

34. The computer program product recited in claim 33, wherein in the computer executable instructions, said first function is a function independent of a transmission energy related to said pixel data and said second function is a function of said transmission energy.

35. The computer program product recited in claim 33, wherein in the computer executable instructions, said first function includes an air-water approximation and said second function includes a water-bone approximation.

36. The computer program product recited in claim 33, wherein said computer executable instructions cause the computer to further perform a step of estimating an effective transmission energy associated with said pixel data.

37. The computer program product recited in claim 36, wherein in the computer executable instructions, said first function is a function independent of said effective transmission energy and said second function is a function of said effective transmission energy.

38. The computer program product recited in claim 33, wherein said computer executable instructions cause the computer to further perform a step of converting said pixel data to Hounsfield units prior to said comparing step.

39. The computer program product recited in claim 33, wherein in the computer executable instructions, said predetermined range comprises a range of Hounsfield units for water to Hounsfield units for air.

40. The computer program product recited in claim 36, wherein said computer executable instructions cause the computer to further perform the steps of:
generating a histogram for said CT image; and
determining a dominant bone peak from said histogram;
and wherein said dominant bone peak is used for estimating said effective transmission energy.

41. The computer program product recited in claim 40, wherein in the computer executable instructions, said first function is a function independent of said effective transmission energy and said second function is a function of said effective transmission energy and a value of said dominant bone peak.

42. The computer program product recited in claim 40, wherein in the computer executable instructions, said first function varies based upon a relationship between an emission energy related to said pixel and a transition energy.

43. The computer program product recited in claim 40, wherein in the computer executable instructions, if no dominant bone peak is determined, said computer executable instructions cause the computer to further perform the steps of:
calculating a Laplacian of said histogram;
determining a local maximum from said Laplacian:
setting said effective transmission energy based on said local maximum; and
setting said dominant bone peak based on said local maximum.

44. A system for generating a linear attenuation coefficient map, comprising:
input means for receiving pixel data;
processing means for comparing a value of the pixel data to a predetermined range, selecting a function based on whether said value is within said predetermined range or outside said predetermined range, and calculating a linear attenuation coefficient from said pixel date using the selected function; and
output means for outputting said calculated linear attenuation coefficient.

45. The system as recited in claim 44, further comprising:
storage means for storing conversion data.

46. The system as recited in claim 44, wherein said processing means calculates a transmission energy of said pixel data, and wherein if said value is within said predetermined range, said processing means selects a function that is independent of said transmission energy related to said pixel data, and if said value is outside said predetermined range, said processing means selects a function that is dependent upon said transmission energy.

47. The system recited in claim 44, wherein if said value is within said predetermined range, said processing means selects a function that includes an air-water approximation, and if said value is outside said predetermined range, said processing means selects a function that includes a water-bone approximation.

48. The system as recited in claim 44, wherein said processing means estimates an effective transmission energy associated with said pixel data.

49. The system as recited in claim 48, wherein said processing means converts said pixel data to Hounsfield units.

50. The system as recited in claim 48, wherein said predetermined range comprises a range of a Hounsfield units value for water to a Hounsfield units value for air.

51. The system as recited in claim 48, wherein said pixel data corresponds to a CT image from a CT device, said processing means generates a histogram for said CT image, determines a dominant bone peak from said histogram, and uses said dominant bone peak for estimating said effective transmission energy.

52. The system as recited in claim 51, wherein if said value is outside said predetermined range, said processing means selects a function based on said effective transmission energy and a value of said dominant bone peak.

53. The system as recited in claim 51, wherein if said value is inside said predetermined range, said processing means selects a function based upon a relationship between an emission energy related to said pixel and a transition energy.

* * * * *